(12) United States Patent
Reinhardt et al.

(10) Patent No.: US 8,900,432 B2
(45) Date of Patent: Dec. 2, 2014

(54) SENSOR ELEMENT HAVING AN INNER ANODE

(75) Inventors: Goetz Reinhardt, Boeblingen (DE); Henrico Runge, Stuttgart (DE); Holger Reinshagen, Bamberg (DE); Lothar Diehl, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 1167 days.

(21) Appl. No.: 12/521,705

(22) PCT Filed: Nov. 22, 2007

(86) PCT No.: PCT/EP2007/062683
§ 371 (c)(1),
(2), (4) Date: Nov. 9, 2010

(87) PCT Pub. No.: WO2008/080706
PCT Pub. Date: Jul. 10, 2008

(65) Prior Publication Data
US 2011/0056270 A1    Mar. 10, 2011

(30) Foreign Application Priority Data
Dec. 29, 2006 (DE) .......... 10 2006 062 060

(51) Int. Cl.
*G01N 27/407* (2006.01)
*G01N 27/41* (2006.01)

(52) U.S. Cl.
CPC .......... *G01N 27/4071* (2013.01); *G01N 27/41* (2013.01)
USPC .......... 204/426; 204/427; 204/428; 73/23.31; 73/23.32

(58) Field of Classification Search
CPC ............ G01N 27/404–27/407; G01N 27/41
USPC .......... 204/421–429; 73/23.31, 23.32
See application file for complete search history.

(56) References Cited

U.S. PATENT DOCUMENTS 5,391,284 A * 2/1995 Hotzel .......................... 204/425
6,301,951 B1 * 10/2001 Lenfers et al. .............. 73/23.31
(Continued)

FOREIGN PATENT DOCUMENTS

DE       199 38 416       3/2000
DE    10 2004 035 826     3/2005
(Continued)

OTHER PUBLICATIONS

"Sensoren im Kraftfahrzeug" [Sensors in the Motor Vehicle], Jun. 2001, p. 112-117.

(Continued)

*Primary Examiner* — Jennifer Dieterle
(74) *Attorney, Agent, or Firm* — Kenyon & Kenyon LLP (57) ABSTRACT

A sensor element, which may be used as Lambda probe and/or inside a Lambda probe, for example, is provided for determining at least one physical property of a gas mixture in at least one gas chamber. The sensor element has at least one first electrode, at least one second electrode and at least one solid state electrolyte, which connects the at least one first electrode and the at least one second electrode. The at least one first electrode and the at least one second electrode are situated inside the sensor element. The at least one second electrode is connected to at least one reference gas chamber via at least one discharge air channel.

22 Claims, 5 Drawing Sheets

(56) References Cited

U.S. PATENT DOCUMENTS

| | | | |
|---|---|---|---|
| 6,306,271 | B1 | 10/2001 | Kato et al. |
| 6,340,419 | B1 * | 1/2002 | Nakae et al. .................. 204/429 |
| 7,922,884 | B2 * | 4/2011 | Strohmaier et al. .......... 204/424 |
| 2003/0106796 | A1 * | 6/2003 | Emmei et al. ................. 204/426 |
| 2003/0136677 | A1 * | 7/2003 | Neumann et al. ............. 204/426 |
| 2003/0188967 | A1 * | 10/2003 | Isitani et al. ................. 204/406 |
| 2005/0034986 | A1 * | 2/2005 | Scheer et al. ................. 204/426 |
| 2005/0145492 | A1 * | 7/2005 | Strohmaier et al. .......... 204/424 |

FOREIGN PATENT DOCUMENTS

| | | |
|---|---|---|
| DE | 103 52 797 | 6/2005 |
| DE | 10 2004 027630 | 1/2006 |
| DE | 10 2005 027225 | 4/2006 |
| DE | 10 2004 057687 | 6/2006 |
| EP | 0 678 740 | 10/1995 |
| JP | 2005-62184 | 3/2005 |
| JP | 2005-510714 | 4/2005 |
| JP | 2006-10673 | 1/2006 |
| JP | 2006-118976 | 5/2006 |
| WO | WO 2005/047841 * | 5/2005 |

OTHER PUBLICATIONS

"T. Baunach et al. : Sauberes Abgas durch Keramiksensoren" [Clean Exhaust Gas Through Ceramic Sensors], Physik Journal 5 (2006) No. 5, p. 33-38.

International Search Report, PCT/EP2007/062683, dated May 29, 2008.

* cited by examiner

SENSOR ELEMENT HAVING AN INNER ANODE

FIELD OF THE INVENTION

The present invention starts out from known sensor elements that are based on electrolytic properties of certain solids, namely the capability of these solids to conduct certain ions.

BACKGROUND INFORMATION

Such sensor elements are used especially in motor vehicles for measuring air/fuel gas mixture compositions. More specifically, sensor elements of this type are used as so-called "lambda probes", and they play an important part in the reduction of pollutants in exhaust gases, both in Otto engines and in Diesel technology.

In combustion technology, the so-called air ratio "lambda" ($\lambda$) generally denotes the ratio of an actually supplied air mass to an air mass theoretically required (i.e., stoichiometric air mass). The air ratio is measured using one or more sensor elements mostly at one or more locations in the exhaust tract of an internal combustion engine. Accordingly, "rich" gas mixtures (i.e. gas mixtures having an excess in fuel) have an air ratio $\lambda < 1$, whereas "lean" gas mixtures (i.e. gas mixtures having a fuel deficiency) have an air ratio $\lambda > 1$. Besides the motor vehicle technology, such and similar sensor elements are also used in other fields of technology (especially in combustion technology), e.g., in aviation technology or in the control of burners, for instance, in heating systems or power plants. Numerous different developments of the sensor elements are known from the related art and described, for instance, in Robert Bosch GmbH: "Sensoren im Kraftfahrzeug" [Sensors in the Motor Vehicle], June 2001, p. 112-117, or in T. Baunach et al.: "Sauberes Abgas durch Keramiksensoren" [Clean Exhaust Gas Through Ceramic Sensors], Physik Journal 5 (2006) No. 5, p. 33-38.

One development is the so-called voltage-jump sensor, whose measuring principle is based on measuring an electrochemical potential difference between a reference electrode exposed to a reference gas and a measuring electrode exposed to the gas mixture to be measured. Reference electrode and measuring electrode are interconnected via the solid state electrolyte; because of its oxygen-ion conducting properties, zirconium dioxide (i.e., yttrium-stabilized zirconium dioxide) or similar ceramics are normally used as solid state electrolyte. Theoretically, the potential difference between the electrodes, especially in the transition between rich gas mixture and lean gas mixture, exhibits a characteristic abrupt change, which can be utilized to measure and/or control the gas mixture composition. Different exemplary embodiments of such voltage jump sensors, which are also known as Nernst cells, are discussed in DE 10 2004 035 826 A1, DE 199 38 416 A1 and DE 10 2005 027 225 A1, for example.

Alternatively or in addition to voltage-jump sensors, so-called "pump cells" are used as well, in which an electrical "pump voltage" is applied to two electrodes connected via the solid state electrolyte, and the "pump current" is measured by the pump cell. In contrast to the principle of the voltage-jump sensors, in the case of pump cells both electrodes are usually in contact with the gas mixture to be measured. In the process, one of the two electrodes is directly exposed to the gas mixture to be measured (usually via a permeable protective layer). As an alternative, this electrode may also be exposed to an air reference. However, the second of the two electrodes is usually implemented in such a way that the gas mixture is unable to reach this electrode directly, but instead must first pass through a so-called "diffusion barrier" in order to reach a cavity adjoining this second electrode. In most cases, a porous ceramic structure having selectively adjustable pore radii is used as diffusion barrier. If lean exhaust gas penetrates this diffusion barrier and enters the cavity, then oxygen molecules are electrochemically reduced to oxygen ions at the second, negative electrode by the pump voltage, transported through the solid state electrolyte to the first, positive electrode, where they are released again in the form of free oxygen. The sensor elements are mostly operated in what is referred to as limit current operation, which means in an operation in which the pump voltage is selected in such a way that the oxygen entering through the diffusion barrier is pumped completely to the counter electrode. In this operation the pump current is approximately proportional to the partial pressure of the oxygen in the exhaust-gas mixture, which is why sensor elements of this type are frequently also referred to as proportional sensors. In contrast to voltage-jump sensors, pump cells are able to be used for the air ratio Lambda across a relatively wide range, so that pump cells are used especially in so-called broadband sensors, for measuring and/or controlling also in the presence of gas mixture compositions beyond $\lambda = 1$.

The afore-described sensor principles for voltage-jump cells and pump cells may advantageously also be used in combination, in what is known as "multicellulars". For instance, the sensor elements may include one or more cells operating according to the voltage-jump sensor principle, and one or more pump cells. One example of a so-called double-cellular is discussed in EP 0 678 740 B1. Using a Nernst cell, the partial oxygen pressure in the afore-described cavity, adjoining the second electrode, of a pump cell is measured, and the pump voltage is corrected by a closed-loop control in such a way that the condition $\lambda = 1$ prevails in the cavity at all times. Different modifications of this multi-cellular design are known.

However, the sensor elements known from the related art having a single-cell system in which two electrodes are exposed to the exhaust gas or the measuring gas frequently show a definite characteristic curve only with lean exhaust gas. In slightly lean operation, however, i.e., when $\lambda$ approaches the value of 1, a deviation of the pump current characteristic curve from the theoretical curve is frequently noticed. Instead of a drop in the pump current at Lambda values that decrease in the direction of the value $\lambda = 1$, a rise in the pump current may often even be seen. Because of this deviation the pump current curve no longer exhibits an unambiguous characteristic from which the air ratio is inferable. This has a negative effect on Lambda sensors to be used in Diesel vehicles, for example, which are operated in slightly lean operation in general.

SUMMARY OF THE INVENTION

The exemplary embodiments and/or exemplary methods of the present invention is based on the idea that the deviation of the pump current from the expected characteristics curve in slightly lean and in the rich range is due to the presence of oxidizable components (rich gas) in the environment of the anode. In this case, instead of the cathode reactions defining the limit current in the lean range, reactions at the anode, which is normally also exposed to the exhaust gas, are decisive. These anode reactions cause a current signal as in lean operation, which is indistinguishable from the current signal because of the reactions taking place at the cathode. Even low quantities of combustible gas (i.e., oxidizable gas components, especially $H_2$) can affect the measuring signal, so that the unambiguous nature of the characteristics curve of the limit current already can no longer be ensured for non-equilibrium exhaust gas (e.g., in Diesel operation) starting at close to $\lambda=1$.

In order to obtain an unambiguous characteristics curve of a sensor element in the range of air $>\lambda\geq1.0$ (i.e., no or only a negligible current signal in the rich range, in particular), the reactions taking place in the rich gas at the anode, such as $$CO+O^{2-}\rightarrow CO_2+2e^-$$

$$H_2+O^{2-}\rightarrow H_2O+2e^-$$

must therefore be prevented.

An essential advantage of the sensor element according to the present invention is that at least one second electrode is provided, which may be able to be operated as anode and which is shielded from oxidizable components from the exhaust gas in that the at least one second electrode is shifted into the interior of the sensor element. The concentrations of the combustible gas in a non-equilibrium Diesel exhaust gas in the proximity of $\lambda=1$, and the excess combustion gases in the rich exhaust gas can no longer influence the Lambda signal in this case since practically no combustion gas conversion is able to take place at the at least one second electrode anymore. Therefore, a sensor element for determining at least one physical characteristic of a gas mixture in at least one gas chamber is provided, for instance a sensor element that is suitable for use as Lambda probe or for use inside a Lambda probe. The sensor element has at least one first electrode, at least one second electrode, and at least one solid state electrolyte connecting the at least one first electrode and the at least one second electrode. With regard to possible materials for the at least two electrodes and the at least one solid state electrolyte, reference may be made to the related art, for example. According to the exemplary embodiments and/or exemplary methods of the present invention, the at least one first electrode and the at least one second electrode are situated inside the sensor element, in contrast to conventional pump cell layer structures (e.g., the pump cell described in Robert Bosch GmbH: "Sensors in the Motor Vehicle", June 2001, page 116), in which the anode is typically exposed to the exhaust gas (directly or via a porous protective layer). "In the interior" is to be understood to denote especially that the at least one first electrode and the at least one second electrode are at least regionally separated from the at least one gas chamber by at least one layer that is impermeable for the gas mixture (e.g., one or more solid state electrolyte layer(s)). Furthermore, at least one discharge air channel is provided, via which the at least one second electrode is connected to at least one reference gas chamber (for instance an engine chamber of a motor vehicle), which is separated from the at least one gas chamber.

One essential advantage of the provided system is that an unambiguous characteristics curve is realizable in the range of air $>\lambda\geq1$. This permits the production of a cost-effective sensor element even without using complex multi-cellular structures (which, however, are realizable as well), which sensor element is suitable also for use in Diesel vehicles.

The at least one discharge air channel may be realized as open discharge air channel, or it may include at least one porous fill element, such as at least one porous fill element on $Al_2O_3$ basis. The at least one discharge air channel may have at least one of the following properties, for example:

the at least one discharge air channel has a rectangular cross-sectional area;

the at least one discharge air channel has a length in the range from 5 mm to 60 mm, which may be in the range from 35 mm to 60 mm;

the at least one discharge air channel has a cross-sectional area in the range from $5\cdot10^{-3}$ mm$^2$ to $240\cdot10^{-3}$ mm$^2$, which may be from $20\cdot10^{-3}$ mm$^2$ to $120\cdot10^{-3}$ mm$^2$.

As in the related art, the at least one first electrode may advantageously be separated from the at least one gas chamber by at least one diffusion barrier. In particular, this diffusion barrier may be a porous, ceramic material, for example, which restricts the subsequent flow of gas mixture to the at least one first electrode, and therefore the limit current of the at least one first electrode. Furthermore, to apply gas mixture to the at least one first electrode, the at least one first electrode may be connected to the at least one gas chamber, for instance via a gas access hole, the at least one gas access hole advantageously penetrating the afore-described gas-impermeable layers that separate the electrodes from the at least one gas chamber.

Moreover, it has been shown to be advantageous if the at least one first electrode (possibly in cooperation with the at least one diffusion barrier), and the at least one second electrode (in cooperation with the at least one discharge air channel and possibly with the at least one porous fill element) are mutually adapted in their limit currents. A limit current or air limit current is to be understood as the specific current that is maximally achievable in air in a given system during cathodic operation of the particular electrode. This is the particular current that corresponds to a situation in which all identifiable gas molecules arriving at the individual electrode are carried away directly via the solid state electrolyte. For example, it has become apparent that the limit current of the at least one second electrode should be lower than the limit current of the at least one first electrode, which may advantageously be achieved by appropriate dimensioning and/or selection of the at least one discharge air channel and/or the at least one porous fill element. This means that the at least one second electrode is shielded in especially effective manner from inwardly diffusing contaminations from the at least one reference gas chamber, e.g., organic contaminants that are present there, which could cause the afore-described rich gas reactions at the anode (and thus a falsification of the current signal). Shielding the at least one second electrode from other contamination that could falsify the potential of the at least one second electrode, for instance, is also realizable in an effective manner by such a selection of the limit current. For example, it has been shown to be especially advantageous if the limit current of the at least one second electrode may be lower than $\frac{1}{50}$ of the limit current of the at least one first electrode and, especially preferred, lower than $\frac{1}{100}$.

The afore-described effective shielding of the at least one first electrode and the at least one second electrode by placing these electrodes in the interior of the sensor is able to be improved advantageously in that at least one reducing electrode is integrated into the sensor element as well. This at least one reducing electrode is advantageously disposed in a layer plane (or in a plurality of layer planes) that does not coincide with a layer plane in which the at least one first electrode and/or the at least one second electrode are/is disposed. The use of the at least one reducing electrode avoids disadvantages that are related to an implementation in which the electrodes lie next to each other.

These disadvantages are, in particular, that the adjacent positioning of the first electrode and the second electrode usually produces an increased inner resistance, and the current density across the electrode is distributed in an inhomogeneous manner. The at least one reducing electrode, which advantageously overlaps the at least one first electrode and/or the at least one second electrode either completely or partially, provides for a "rerouting" of the flow through the at least one solid state electrolyte, and by shortening the distances, for a considerably reduction of the internal resistance and thus reduced pump voltages. Various types of layer structures are realizable. Also, it is possible to use the at least one reducing electrode, which advantageously is implemented as "floating" electrode (not contacted), for "trimming" the internal resistance of the sensor element during the production; the shape and/or the size of the at least one reducing electrode are/is adapted by an appropriate cutting and/or ablation process, until the internal resistance of the sensor element has attained a desired value. This makes it possible to realize a reliable, cost-effective production method of a sensor element, as well as high precision of the sensor elements produced in this manner.

In particular, the described sensor element is able to be operated in such a way (e.g., by electronic circuit elements integrated into the sensor element and/or external electronic elements) that a pump voltage, especially between 100 mV and 1.0 V, which may be between 300 mV and 600 mV and, especially preferred, between 600 mV and 700 mV, is applied between the at least one first electrode and the at least one second electrode, at least one pump current being measured, which flows between the at least one first electrode and the at least one second electrode. The at least one first electrode may be switched as pump cathode at least intermittently, and the at least one second electrode is switched as pump anode at least intermittently. However, a change (e.g., intermittent change) of the polarities is possible as well, for instance within the framework of alternating polarities in a closed-loop control. A different type of wiring configuration is also conceivable.

Exemplary embodiments of the present invention are shown in the drawing and explained in greater detail in the following description.

DETAILED DESCRIPTION

Figure 1:
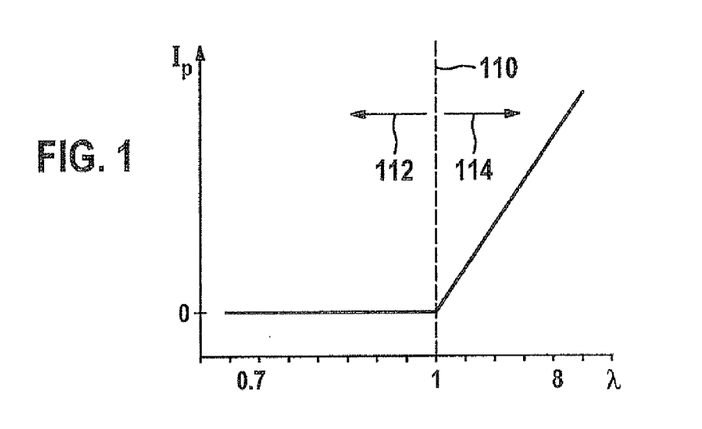
FIG. 1 shows a characteristics curve of a pump current.

FIG. 1 schematically illustrates a curve of a pump current $I_p$ as a function of the air ratio $\lambda$ of a gas mixture. This is the expected curve of the characteristic for a design according to the present invention of a sensor element having a pump anode, which is completely shielded from the combustion gas. Perpendicular dashed line 110 denotes the value $\lambda=1$, which separates rich range 112 from lean range 114. It is noticeable that the characteristic to be expected exhibits a linear rise in the range $\lambda>1$ and assumes the value of 0 in the rich range, i.e. for $\lambda<1$.

If the pump electrode were not shielded from the combustion gas as provided by the present invention, then a non-disappearing pump current would occur, especially in rich range 112, which can be attributed to the afore-described rich gas reactions at the pump anode. A deviation from the linear characteristic of the characteristic curve would already be noticeable in a slightly lean range, i.e., in range 114 near $\lambda=1$.

Figure 2:
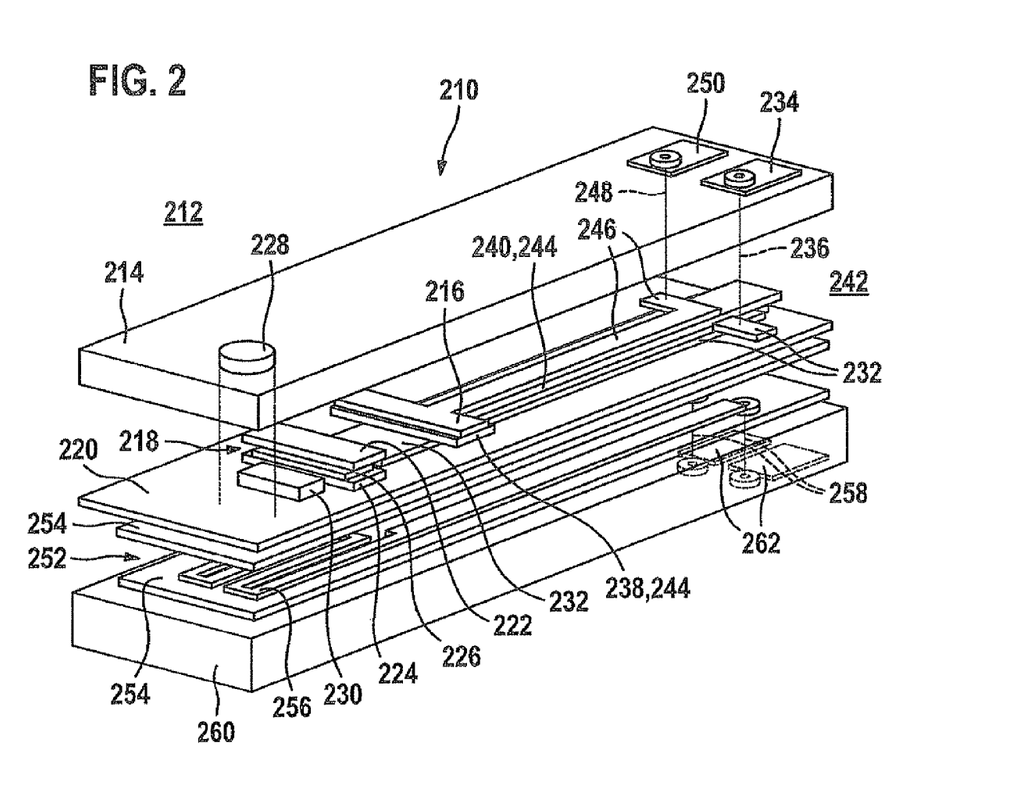
FIG. 2 shows a layer structure of a sensor element designed as single cell, having an internal pump cathode and internal pump anode and superposed supply leads.

FIG. 2 shows a first exemplary embodiment of a sensor element 210 according to the present invention in a perspective representation of the layer structure. This sensor element 210 is a single cell, which is able to be realized in a relatively simple and cost-effective manner. For instance, the described sensor element may be used as limit current lean probe for analyzing gas mixtures in a gas chamber 212.

On the side facing gas chamber 212, sensor element 210 has a first solid state electrolyte 214, for instance an yttrium-stabilized zirconium dioxide electrolyte. Inside a layer plane on the side of solid state electrolyte 214 that faces away from gas chamber 212, solid state electrolyte 214 is in contact with a pump anode 216 (e.g., a platinum electrode and/or an oxide electrode) and a pump cathode 218, pump anode 216 and pump cathode 218 being disposed next to one another. As described earlier, in this and also in the following exemplary embodiments the at least one first electrode is connected as pump cathode (218) and the at least one second electrode is connected s pump anode (216). However, as also described already, other types of wiring are conceivable as well, e.g., an at least brief polarity reversal. A second solid state electrolyte 220 is situated underneath pump anode 216 and pump cathode 218, so that pump anode 216 and pump cathode 218 are embedded between the two solid state electrolytes 214, 220. While pump anode 216 is designed only as single electrode, pump cathode 218 optionally has a first partial cathode 222 and a second partial cathode 224 in this exemplary embodiment, first partial cathode 222 contacting solid state electrolyte 214 lying on top, and second partial cathode 224 contacting second solid state electrolyte 220 lying at the bottom. However, both partial cathodes 222, 224 are connected in electrically conductive manner, so that they act as single pump cathode 218, but with an enlarged surface. This makes it possible to reduce the internal resistance of sensor element 210. Optionally, pump anode 216 may also be designed as double electrode (cf. the development in FIG. 3 below, for example).

A cathode cavity 226 is provided between the two partial cathodes 222, 224. Via a gas access hole 228 in the upper solid state electrolyte 214, gas mixture from gas chamber 212 is able to penetrate cathode cavity 226. A diffusion barrier 230, which, as described earlier, has a porous ceramic material and restricts the limit current of pump cathode 218, is provided between gas access hole 228 and cathode cavity 226. Pump cathode 218 is electrically contacted by a cathode lead 232, which is situated on lower solid state electrolyte 220. Via a cathode lead 234 on the top surface of solid state electrolyte 214, and via an electric plated contacting 236, pump cathode 218 is connectable to a corresponding electronic circuit (not shown in FIG. 2), and a voltage may be applied to it, for instance.

Provided underneath pump anode 216 is an anode cavity 238, which is connected to a reference gas chamber 242 that is separated from gas chamber 212 via a discharge air channel 240. Anode cavity 238 and discharge air channel 240 are filled with a porous fill element 244 on $Al_2O_3$ basis, which is permeable for oxygen. Pump anode 216 is electrically contacted via an anode lead 246, and via an additional electric plated contacting 248 in solid state electrolyte 214, it is connected to an anode lead 250 disposed on the top surface of solid state electrolyte 214. Via this anode lead 250, pump anode 216 is connectable to the afore-described electronic device, for instance, so that a voltage is able to be applied between pump anode 216 and pump cathode 218, for example, and/or a pump current can be measured. In the exemplary embodiment according to FIG. 2, anode lead 246 and cathode lead 232 are disposed on top of one another. An electric insulation of pump anode 216 or anode lead 246 with respect to cathode lead 232 is implemented by porous fill element 244, which has electrically non-conductive properties.

Underneath second solid state electrolyte 220 there is a heating element 252, which includes a heat resistor element 256 embedded between two insulator foils 254. Via plated contactings 258 in a carrier substrate 260 (e.g., another solid state electrolyte), heat resistor element 256 is able to be electrically contacted via heating connections 262 on the side of carrier substrate 260 facing away from gas chamber 212, and a heating current may be applied to it. For example, this heating current is able to be controlled by a closed-loop control, which sets a constant internal resistance of sensor element 210, for instance.

With the aid of the exemplary embodiment of a sensor element 210 described in FIG. 2, the pump current characteristic curve shown in FIG. 1 is able to be realized in principle. When used as Lambda probe, in lean range 114 a pump current is measured according to the partial oxygen pressure, and no current is measured in rich range 112 since no free oxygen is available and the selected pump voltage advantageously lies below the decomposition voltage of the water. Thus, no combustion gas oxidation is able to occur at the inner, shielded combustion-gas-blind pump anode 216. This makes it possible to realize a cost-effective sensor element 210 designed as single-cell element, which also is suitable for use in Diesel vehicles.

Figure 3:
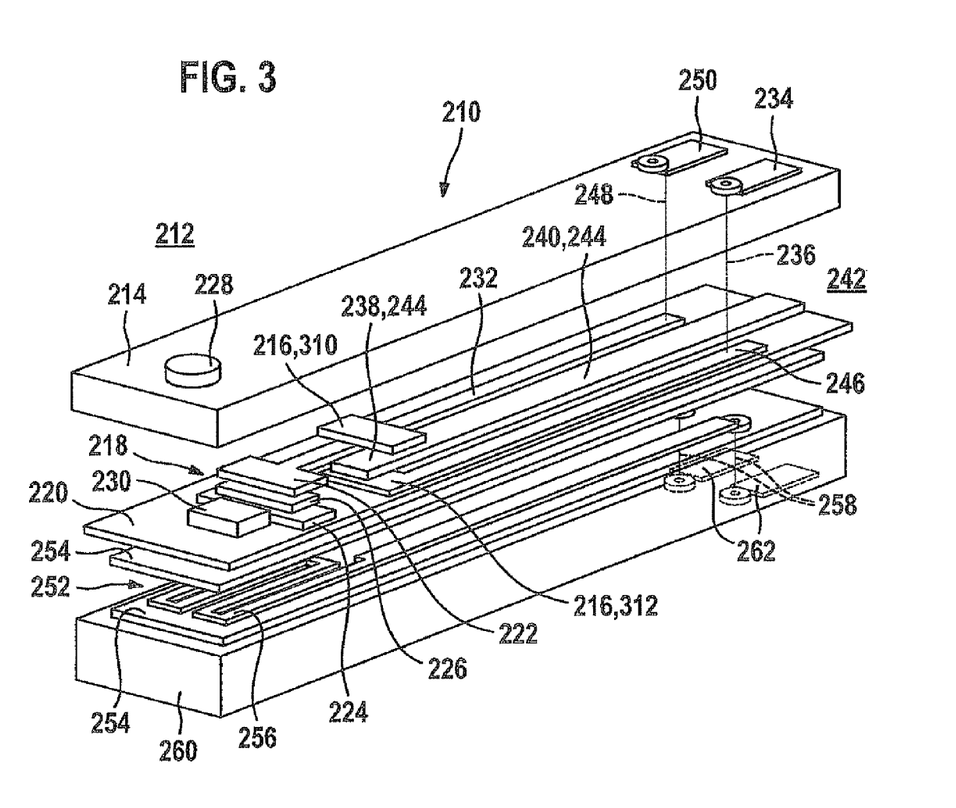
FIG. 3 shows a sensor element according to FIG. 3, but with supply leads that lie next to each other.

FIG. 3 shows a perspective layer drawing of a second exemplary embodiment of a sensor element 210 according to the present invention. The design largely corresponds to the exemplary embodiment of FIG. 2, so that reference is made to this exemplary embodiment with regard to the individual elements. In contrast to the exemplary embodiment according to FIG. 2, however, in the exemplary embodiment according to FIG. 3 it is not only the case that pump cathode 218 has two partial cathodes 222, 224, but pump anode 216, as well, is designed in two parts, having a first partial anode 310 lying on top, which contacts upper solid state electrolyte 214, and a second partial anode 312 lying at the bottom, which contacts solid state electrolyte 220 disposed below. Once again partial anodes 310, 312 are electrically interconnected in conductive manner, analogously to partial cathodes 222, 224. The advantage of this system, as described above, is the reduced internal resistance of sensor element 210 since pump currents are now able to be effectively routed through upper solid state electrolyte 214 and lower solid state electrolyte 220.

The two partial anodes 310, 312 are separated from one another by anode cavity 238, which again is filled with porous fill element 244 analogously to FIG. 3. In the exemplary embodiment according to FIG. 3 as well, analogously to FIG. 2, anode cavity 238 is connected to reference gas chamber 242 via discharge air channel 240, which is likewise filled with porous fill element 244.

Also in contrast to the exemplary embodiment of FIG. 2, in the exemplary embodiment of sensor element 210 according to FIG. 3, there is no superposed placement of electrode leads 232, 246, by which pump cathode 218 and pump anode 216 are contacted. Instead, anode lead 246 and cathode lead 232 are disposed next to each other on lower solid state electrolyte 220, and discharge air channel 240 lies centered between the two electrode leads 232, 246 and extends parallel thereto. Analogously to the exemplary embodiment in FIG. 2, the contacting of electrode leads 232, 246 is implemented via electrode leads 234, 250. As far as the additional components and the method of functioning are concerned, reference is made to the above description.

Figure 4A:
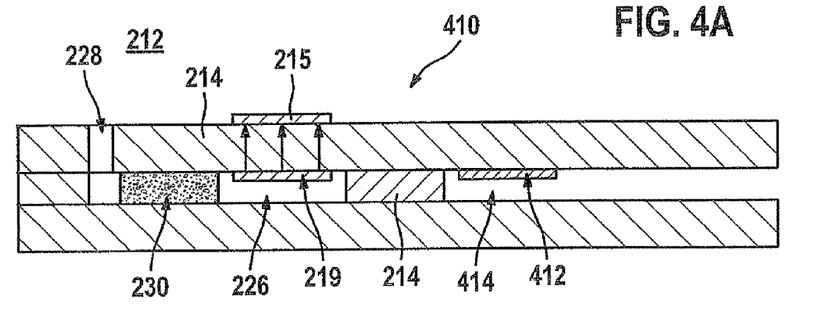
FIG. 4A shows a configuration of a broadband sensor according to the related art.
Figure 4B:
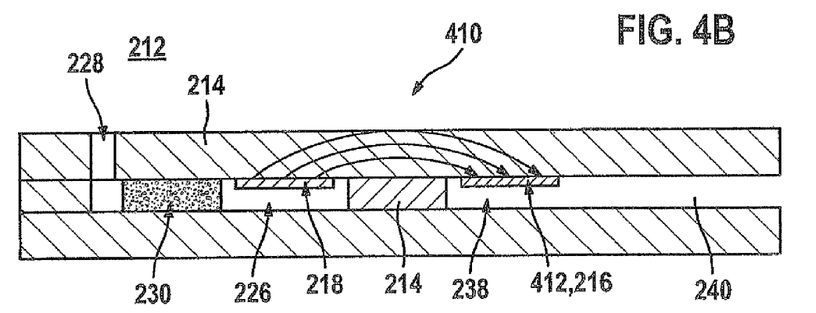
FIG. 4B shows an example of a sensor element designed as lean sensor.

Components having electrodes that lie next to each other frequently exhibit considerable internal resistance, which often requires high pump currents, which in turn pose a higher risk of decomposition of water. The problem of increased internal resistance is going to be described with the aid of two sensor elements 410, which are shown in FIGS. 4A and 4B. FIG. 4A shows a configuration known from the related art, in which, analogously to the exemplary embodiments in FIGS. 2 and 3, a subsequent transport of oxygen from gas chamber 212 into electrode cavity 226 is blocked in front of pump electrode 219 (which is usually also referred to as "inner pump electrode" IPE). Counter electrode 215 is situated on the outside-lying side of solid state electrolyte 214 facing gas chamber 212, across from IPE 219. This counter electrode 215 is frequently also referred to as "outer pump electrode" APE. As described above, the polarity between pump cathode 219 and pump anode 215 is also able to be alternated during closed-loop control operation, so that the term "pump electrode" would have to be used without polarity differentiation. The signal from sensor element 410 is the oxygen flow that is flowing between the two pump electrodes 215, 219.

Furthermore, a reference electrode 412 is provided, which is situated in an air reference chamber 414 separated from IPE cavity 226 (or in an air reference channel). The pump voltage between the two pump electrodes 215, 219 is regulated in such a way that a specific voltage (Nernst voltage) is applied between IPE 219 and reference electrode 412. This control voltage is selected such that an essentially stoichiometric mixture is present inside IPE cavity 226, i.e., a mixture having $\lambda=1$. To this end, in the case of lean gas mixtures, oxygen is pumped out of the cavity while in the case of rich gas mixtures oxygen is pumped into the cavity in order to combust the rich components that enter. The polarity of the voltage between IPE 219 and APE 215 is selected accordingly. The current direction has a sign change in the transition from rich gas mixtures to lean gas mixtures and can be measured unambiguously across the entire range of $\lambda$.

For applications in the lean range, i.e., for $\lambda>1$, a simpler configuration than shown in FIG. 4A may be selected, which is shown in FIG. 4B. In illustrated sensor element 410, the outer pump electrode, and thus one lead contact, is omitted.

The oxygen is pumped from the inner pump electrode (pump cathode 218) to the removal electrode or reference electrode 412, which thus simultaneously acts as pump anode 216. It is important in this context that the gas composition at reference electrode 412 varies only negligibly during operation so that undesired secondary reactions at pump cathode 218 are avoided. In such an operation an unambiguous characteristic curve for $\lambda>1$ is able to be realized.

Thus, sensor element 410 illustrated in FIG. 4B already corresponds to the sensor element of the present invention according to one of the exemplary embodiments in FIG. 2 or 3, inasmuch as adjacently positioned electrodes 216, 218 in the interior of sensor element 410 are already realized in this case. The adjacently disposed electrode system according to FIG. 4B is relatively easy to realize from the standpoint of production engineering. However, this electrode system is disadvantageous inasmuch as, due to the laterally offset electrodes 216, 218, the electric resistance of solid state electrolyte 214 is considerably higher than in the system according to the related art in FIG. 4A having pump electrodes 216, 218 that lie on top of each other. Relatively high currents are flowing especially in oxygen-rich gases (e.g., air), which, via Ohm's law, lead to relatively high voltage losses in solid state electrolyte 214 (e.g., a $ZrO_2$ ceramic) and the electrodes. Therefore, high pump voltages must be applied between electrodes 216, 218, which, however, in turn have the result that close to $\lambda=1$, oxygen is obtained not only from the oxygen molecules of the gas mixture from gas chamber 228, but also from a decomposition of water and carbon dioxide and is indicated as corresponding pump current. This cross sensitivity is one of the reasons why even in a placement according to FIG. 4B with a completely shielded anode 216, a falsification of the pump current characteristic is frequently seen in the lean range when approaching $\lambda=1$. Therefore, the characteristic may generally indeed be unambiguous because of shielded pump anode 216, but it exhibits an increased tolerance in the proximity of $\lambda=1$. FIGS. 5 through 9 therefore show further improved specific embodiments of sensor elements 210, which effectively avoid the described problem with the internal resistance. One core idea concerns the use of at least one reducing electrode 510, which is disposed on a side of solid state electrolyte 214 lying opposite the side on which pump cathode 218 and pump anode 216 are situated. This shortens the current paths considerably, and thereby reduces the internal resistance.

Figure 5:
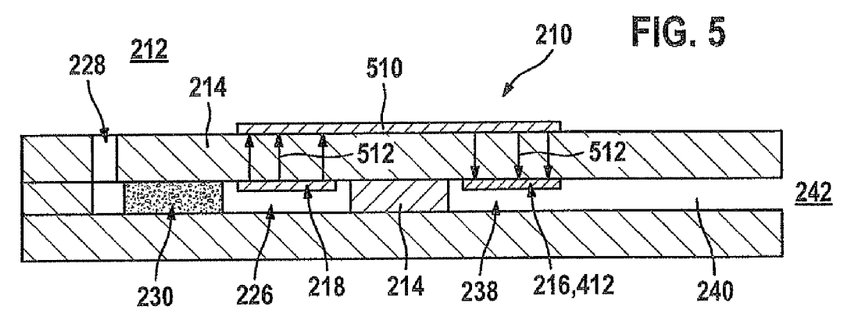
FIG. 5 shows a sensor element having a reducing layer.
Figure 6:
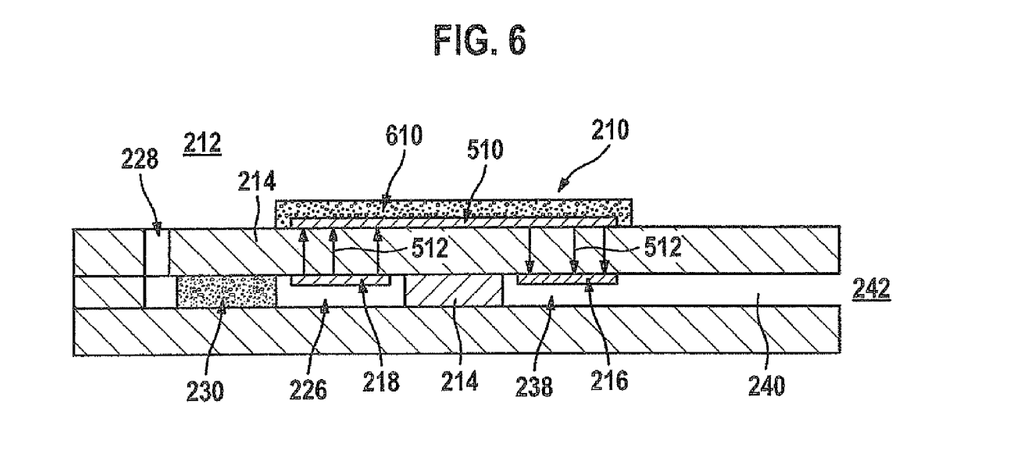
FIG. 6 shows the sensor element according to FIG. 5 having a protective layer in addition.
Figure 7:
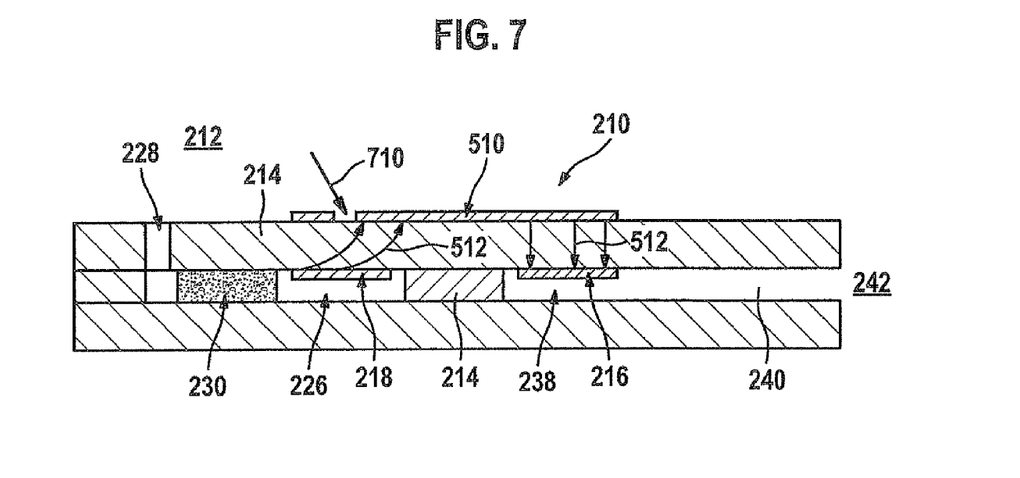
FIG. 7 shows a method for correcting the internal resistance of the sensor element according to FIG. 5.

FIGS. 5 through 7 show exemplary embodiments in which reducing electrode 510 is situated on the side of upper solid state electrolyte 214 facing gas chamber 212, whereas pump anode 216 and pump cathode 218 lie next to each other on the side of solid state electrolyte 214 facing away from gas chamber 212. Reducing electrode 510 is electrically not contacted ("floating"), so that the advantage of having only two electrode leads 234, 250 (cf. FIGS. 2 and 3) is retained. In oxygen-rich gases, this opens up an additional flow path. The oxygen flow, which is symbolically denoted by 512 in FIGS. 5 though 7, first flows from pump cathode 218 (inner pump electrode, IPE) to reducing electrode 510, where it escapes in the form of oxygen. In another location of reducing electrode 510 oxygen is reincorporated and flows to pump anode 216 (which has assumed the function of reference electrode 412). Because of reducing electrode 510, the resistance of the solid state electrolyte is able to be reduced, typically by a factor of 2 to 3, as compared with the system according to FIG. 4B without reference electrode 412. Thus, it comes into the range of the system according to FIG. 4A. The size of reducing electrode 510 in the exemplary embodiment according to FIG. 5 has been selected such that a projection of reducing electrode 510 into the plane of pump cathode 218 or pump anode 216 covers both electrodes 216, 218. Other forms of reducing electrodes 510 may be selected as well.

FIG. 6 shows sensor element 210 according to FIG. 5 in a slightly modified form. In this instance, reducing electrode 510, which is likewise disposed on the side of the solid state electrolyte facing gas chamber 212, is shielded from gas chamber 212 by a porous protective layer 610. This porous protective layer 610, for which conventional APE shielding materials may be utilized, for example, permits the flow-off of released oxygen molecules above pump cathode 218 into gas chamber 212, for one. In the reverse, in the region above pump anode 216, porous protective layer 610 allows the penetration of oxygen and thus again an incorporation of oxygen ions into solid state electrolyte 214. In all other respects, the exemplary embodiment of sensor element 210 in FIG. 6 corresponds to the design in FIG. 5. Protective layer 610 also prevents increased ageing of electrode 510 due to ash or electrode toxins in the exhaust gas. The limit current of protective layer 610 should be higher than the limit current of diffusion barrier 230.

In FIG. 7, sensor element 210 according to the exemplary embodiment in FIG. 5 is shown in slightly modified manner; an advantage of using a reducing electrode 510 is described at the same time. For instance, a method for producing sensor element 210 is described, in which the size and/or the shape of reducing electrode 510 are/is corrected retroactively (or during a production step). A laser-cutting method using a laser beam 710 is used in this exemplary embodiment. A pulsed Nd:YAG laser, for example, may be used for this purpose. Other types of lasers are able to be used as well, such as a gas laser, both in pulsed and in continuous operation.

The method is based on the fact that the temperature regulation by heating element 252 (which is not shown in FIGS. 4A through 7 for reasons of simplification) usually takes place via the internal resistance of solid state electrolyte 214 measured at a high frequency. At these frequencies (typically 1 to 10 kHz, which may be approx. 3 kHz), the electrode resistors are short-circuited via the high capacitances. By adapting plated-through reducing electrode 510 by the laser cut, the internal resistance of the solid state electrolyte or the internal resistance of sensor element 210 is able to be adjusted retroactively. This makes it possible to reduce the temperature variations of sensor elements 210, which are regulated to a constant internal resistance, to a considerable extent.

Following the laser correction illustrated in FIG. 7, additional production steps may ensue, so that, analogously to FIG. 2, a porous protective layer 610, for example, is in turn able to be applied on a reducing electrode 510 corrected in this manner. Additional method steps may also be inserted before the illustrated steps and between the steps, and method steps may be implemented repeatedly. This enables the production of highly precise sensor elements 210 in a cost-effective manner, which are suitable also for Diesel applications, for example.

Figure 8:
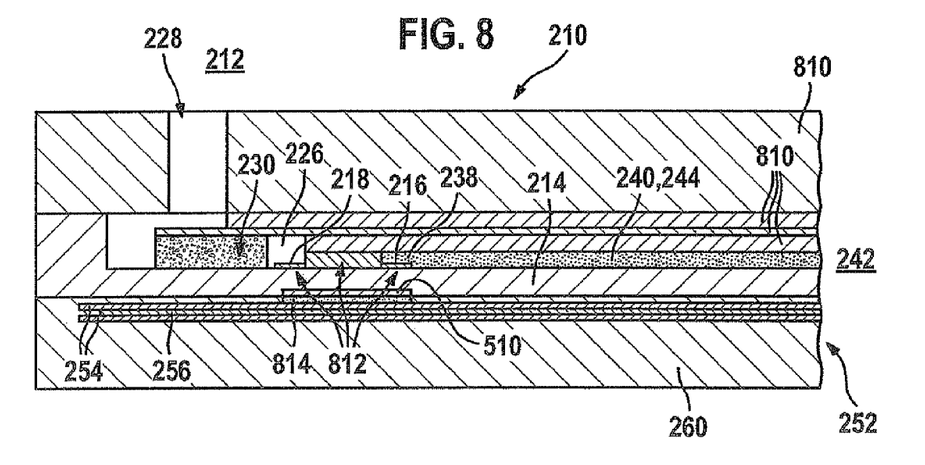
FIG. 8 shows a sensor element having an internal reducing electrode disposed on a heating element.

FIG. 8 shows an exemplary embodiment of a sensor element 210, which, for one, further develops the core idea of inner pump electrodes 216, 218, and the idea of reducing electrode 510, for another. Once again, a pump cathode 218 having a cathode cavity 226 is provided, as well as a pump anode 216 having an anode cavity 238, the pump anode being disposed parallel to pump cathode 218. Anode cavity 238 is again connected to a reference gas chamber 242 via a discharge air channel 240. Anode cavity 238 and discharge air channel 240 may again be filled with a porous fill element 244, for example. Pump cathode 218 and pump anode 216 are disposed next to one another on a solid state electrolyte 214. Via a diffusion barrier 230 and a gas access hole 228, cathode cavity 226 in turn is connected to gas chamber 212, in which the gas mixture composition to be analyzed is situated. To this extent, as far as the method of functioning of sensor element 210 is concerned as well as its configuration, reference can for the most part be made to the above exemplary embodiments according to FIGS. 2 and 3, for example.

Once again, a reducing electrode 510 is provided on a side of solid state electrolyte 214 that lies opposite from electrodes 216, 218, analogously to the above exemplary embodiments according to FIGS. 5 through 7. However, in contrast to the exemplary embodiments illustrated above, reducing electrode 510 in the exemplary embodiment according to FIG. 8 is situated in the interior of sensor element 210, on a side of solid state electrolyte 214 facing away from gas chamber 212. This reducing electrode 510 is in the immediate vicinity of heating element 252, which may be designed analogously to the afore-described exemplary embodiments according to FIGS. 2 and 3. Because of this directly adjacent placement, reducing electrode 510 may have a higher temperature (operating temperatures of approx. 780° C. are typically used) than in a placement of reducing electrode 510 on the top surface of solid state electrolyte 214. This considerably increases the electric conductivity and the kinetics of the reducing electrode (which means a removal or incorporation of oxygen, in particular).

A further advantage of the design according to FIG. 8 results from the fact that the mechanical stability of sensor element 210 according to FIG. 8 is essentially realized by additional support layers 810, which may have different characteristics with regard to the material selection and properties. For example, it is possible again to provide foils for this purpose, such as electrolyte foils, like in the afore-described exemplary embodiments as well, for instance. Intermediate foils may be used as well, for example for effectively shielding diffusion barrier 230 and cathode cavity 226 from gas chamber 212. On the other hand, actual solid state electrolyte 214 may be applied as foil and/or also as (e.g., ceramic) printed layer, or using other types of layer technologies that permit a precisely adjustable, low clearance between reducing electrode 510 and electrodes 216, 218. In this way the electric resistance of pump cell 812, made up of solid state electrolyte 214 and electrodes 216, 218, is able to be reduced to a greater extent than when placing reducing electrode 510 on the top surface of sensor element 210, where an electrolyte foil typically separates reducing electrode 510 from pump electrodes 216, 218.

Another advantage of the system from FIG. 8 is that the effectiveness of reducing electrode 510 is not affected by exhaust gas. To this end, as illustrated in FIG. 8, it is possible to place a gas buffer space 814 between reducing electrode 510 and heating element 252, for example. This gas buffer space 814 may again be in the form of a cavity, for instance, and/or be filled with a porous material. Gas buffer space 814 permits a local oxygen removal or oxygen incorporation at reducing electrode 510. This gas buffer space 814 may be completely shielded from, for example, gas chamber 212 and/or reference gas chamber 242. In this way, the potential of reducing electrode 510, in particular, is unaffected by the exhaust-gas composition, and reducing electrode 510 is largely resistant to toxins. By shielding reducing electrode 510 from the gas mixture, it is also possible to use redox-instable alternative electrodes to the usually employed platinum electrodes, such as conductive oxides, e.g., LSM perovskite (LSM: lanthanum strontium manganate) or similar materials.

Figure 9:
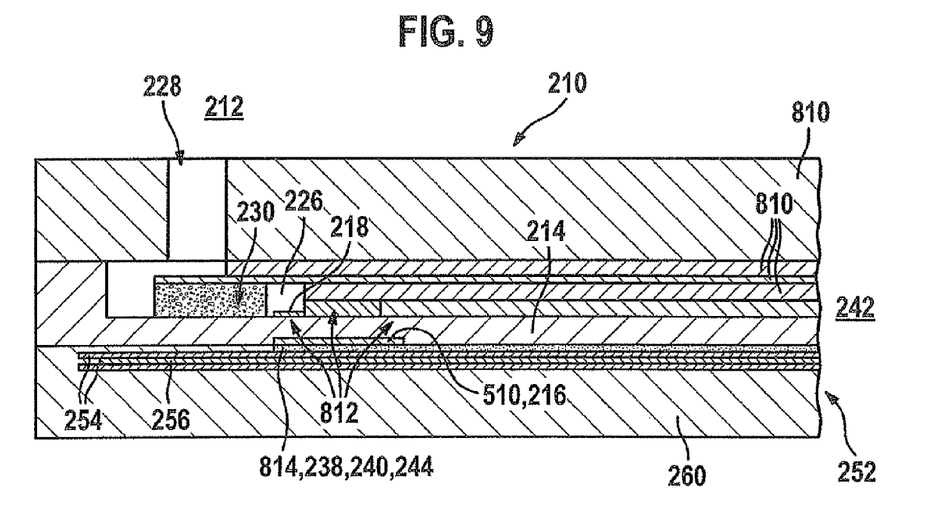
FIG. 9 shows a sensor element according to FIG. 8 having a combined reducing electrode and removal electrode.

In addition, it should be mentioned that reducing electrode 510 and removal electrode 216 may also be combined. An electric contacting of reducing electrode 510 and the linking of reducing electrode 510 to discharge air channel 240 therefore causes it to turn into the removal electrode. This corresponds to a superposed system of incorporation and removal electrode. This exemplary embodiment is shown in FIG. 9, which essentially corresponds to the exemplary embodiment of FIG. 8 in all other respects, so that reference is made to the above description of this figure. In this context, as shown in FIG. 9, discharge air channel 240 may be placed underneath reducing electrode 510 and combined with gas buffer space 814.

What is claimed is:

1. A sensor element for determining at least one physical property of a gas mixture inside at least one gas chamber, in particular for determining an oxygen concentration of an exhaust gas of an internal combustion engine, comprising:
at least one first electrode;
at least one second electrode; and
at least one solid state electrolyte connecting the at least one first electrode and the at least one second electrode;
wherein the at least one first electrode and the at least one second electrode are situated within the sensor element, and the at least one second electrode is connected to at least one reference gas chamber via at least one discharge air channel, and
wherein the at least one air discharge channel is configured to ensure that a limit current of the at least one second electrode is lower than a limit current of the at least one first electrode.

2. The sensor element of claim 1, wherein the at least one discharge air channel has at least one porous fill element, which is based on $Al_2O_3$.

3. The sensor element of claim 1, wherein the at least one first electrode is separated from the at least one gas chamber by at least one diffusion barrier.

4. The sensor element of claim 1, wherein the at least one discharge air channel has at least one of the following characteristics:
(i) the at least one discharge air channel has a rectangular cross-sectional area;
(ii) the at least one discharge air channel has a length in the range from 5 mm to 60 mm; and
(iii) the at least one discharge air channel has a cross-sectional area in the range from $5 \cdot 10^{-3}$ $mm^2$ to $240 \cdot 10^{-3}$ $mm^2$.

5. The sensor element of claim 1, further comprising:
a solid state electrolyte facing the at least one gas chamber, having on a side of the solid state electrolyte facing away from the at least one gas chamber, the second electrode and the first electrode situated next to each other and contacting the solid state electrolyte, wherein a layer configuration has at least one of the following features:
(i) the first electrode and the second electrode are contacted by leads situated essentially parallel to the solid state electrolyte, the leads being disposed essentially on top of each other, and the leads being insulated from each other by the at least one discharge air channel or by the at least one porous fill element;
(ii) the first electrode and the second electrode are contacted by leads situated essentially parallel to the solid state electrolyte, the leads being disposed essentially next to each other, and the leads being insulated from each other by the at least one discharge air channel or by the at least one porous fill element;
(iii) at least one gas access hole is provided in the solid state electrolyte so as to connect the first electrode with the at least one gas chamber;
(iv) at least one second electrode cavity is provided above and/or underneath the second electrode;
(v) at least one first electrode cavity is provided at least one of above and underneath the first electrode;
(vi) at least one second solid state electrolyte is provided underneath the first electrode and the second electrode, wherein at least one of the first electrode and the second electrode contacts the at least one second solid state electrolyte;
(vii) at least one second solid state electrolyte is provided underneath the first electrode and the second electrode, the first electrode having at least one first partial electrode contacting the solid state electrolyte, and at least one second partial electrode contacting the at least one second solid state electrolyte, the at least one first partial electrode and the at least one second partial electrode being connected in electrically conductive manner, and at least one first electrode cavity is provided preferably between the at least one first partial electrode and the at least one second partial electrode;

(viii) at least one second solid state electrolyte is provided underneath the first electrode and the second electrode, the second electrode having at least one first partial electrode contacting the solid state electrolyte, and at least one second partial electrode contacting the at least one second solid state electrolyte, the at least one first partial electrode and the at least one second partial electrode being interconnected in electrically conductive manner, and at least one second electrode cavity is provided preferably between the at least one first partial electrode and the at least one second partial electrode; and (ix) the sensor element has at least one heating element.

6. The sensor element of claim 1, further comprising:
at least one reducing electrode, which contacts the at least one solid state electrolyte, the at least one reducing electrode being disposed in a layer plane that does not coincide with a layer plane in which the at least one first electrode and the at least one second electrode are disposed.

7. The sensor element of claim 6, wherein a perpendicular projection of the at least one reducing electrode into a layer plane in which at least one of the at least one first electrode and the at least one second electrode is disposed, has an overlap with at least one of the at least one first electrode and the at least one second electrode.

8. The sensor element of claim 6, wherein a perpendicular projection of the at least one reducing electrode into the layer plane in which at least one of the at least one first electrode and the at least one second electrode is disposed, covers at least one of the at least one first electrode and the at least one second electrode.

9. The sensor element of claim 6, wherein, when a pump voltage is applied between the at least one first electrode and the at least one second electrode, an ion flow flows through the at least one solid state electrolyte from the at least one second electrode to the at least one reducing electrode, and from the at least one reducing electrode to the at least one first electrode, or vice versa.

10. The sensor element of claim 6, wherein the at least one reducing electrode is not a contacted electrode.

11. The sensor element of claim 6, wherein the at least one reducing electrode is situated in a deeper-lying layer plane than the at least one first electrode and the at least one second electrode.

12. The sensor element of claim 6, further comprising at least one heating element wherein the at least one reducing electrode is situated between the at least one heating element and the at least one solid state electrolyte.

13. The sensor element of claim 6, wherein the at least one reducing electrode is in connection with at least one gas buffer space for intermediately storing gas.

14. The sensor element of claim 6, wherein the at least one reducing electrode is situated on a side of the at least one solid state electrolyte facing the at least one gas chamber.

15. The sensor element of claim 1, wherein the at least one physical property of a gas mixture inside at least one gas chamber is an oxygen concentration of an exhaust gas of an internal combustion engine.

16. The sensor element of claim 1, wherein the limit current of the at least one second electrode is lower than $\frac{1}{50}$ of the limit current of the at least one first electrode.

17. The sensor element of claim 1, wherein the limit current of the at least one second electrode is lower than $\frac{1}{100}$ of the limit current of the at least one first electrode.

18. The sensor element of claim 1, wherein the at least one discharge air channel has at least one of the following characteristics:
(i) the at least one discharge air channel has a rectangular cross-sectional area;
(ii) the at least one discharge air channel has a length in the range from 35 mm to 60 mm; and
(iii) the at least one discharge air channel has a cross-sectional area in the range from $20 \cdot 10^{-3}$ mm$^2$ to $120 \cdot 10^{-3}$ mm$^2$.

19. The sensor element of claim 6, wherein the at least one reducing electrode is situated on a side of the at least one solid state electrolyte facing the at least one gas chamber, the at least one reducing electrode being separated from the at least one gas chamber by at least one protective layer.

20. The sensor element of claim 1, wherein the at least one discharge air channel has a rectangular cross-sectional area.

21. The sensor element of claim 1, wherein a length of the at least one discharge air channel is in a range from 35 mm to 60 mm.

22. The sensor element of claim 1, wherein the at least one discharge air channel has a cross-sectional area in a range from $20 \cdot 10^{-3}$ mm$^2$ to $120 \cdot 10^{-3}$ mm$^2$.

* * * * *